(12) United States Patent
Dannoritzer et al.

(10) Patent No.: US 11,123,092 B2
(45) Date of Patent: Sep. 21, 2021

(54) HANDLE DEVICE

(71) Applicant: STERIS Deutschland GmbH, Cologne (DE)

(72) Inventors: Axel Dannoritzer, Tuttlingen (DE); Stefan Rauch, Tuttlingen (DE); Harald Fuchs, Tuttlingen (DE); Gerlinde Klaiber, Hausen (DE); Julian Dannoritzer, Wurmlingen (DE)

(73) Assignee: STERIS Deutschland GmbH, Cologne (DE)

( * ) Notice: Subject to any disclaimer, the term of this patent is extended or adjusted under 35 U.S.C. 154(b) by 145 days.

(21) Appl. No.: 15/544,550

(22) PCT Filed: Oct. 29, 2015

(86) PCT No.: PCT/EP2015/075121
§ 371 (c)(1),
(2) Date: Oct. 16, 2017

(87) PCT Pub. No.: WO2016/116179
PCT Pub. Date: Jul. 28, 2016

(65) Prior Publication Data
US 2018/0064457 A1    Mar. 8, 2018

(30) Foreign Application Priority Data

Jan. 22, 2015  (DE) .................... 10 2015 100 945 U

(51) Int. Cl.
*A61B 17/28*    (2006.01)
*A61B 17/16*    (2006.01)
(Continued)

(52) U.S. Cl.
CPC ...... *A61B 17/2841* (2013.01); *A61B 17/1611* (2013.01); *A61B 17/2909* (2013.01);
(Continued)

(58) Field of Classification Search
CPC ............... A61B 10/06; A61B 17/1611; A61B 17/2841; A61B 17/2909
See application file for complete search history.

(56) References Cited

U.S. PATENT DOCUMENTS 5,584,844 A * 12/1996 Weisshaupt ........ A61B 17/1611
606/170
6,077,290 A *  6/2000 Marini ................... A61B 17/29
600/564

(Continued)

FOREIGN PATENT DOCUMENTS

DE        29619246 U1    1/1997
DE     102008058207 A1    5/2010
(Continued)

OTHER PUBLICATIONS

Search Report dated Nov. 5, 2015 issued in corresponding DE patent application No. 10 2015 100 945.5 (and partial English translation).

(Continued)

*Primary Examiner* — Sarah A Simpson
(74) *Attorney, Agent, or Firm* — Posz Law Group, PLC

(57) ABSTRACT

A handle device, in particular a surgical-tool handle device, with a first handle element and a second handle element, and with a shear joint by means of which the two handle elements are connected pivotably and separably, and with a coupling unit, which is configured to keep the two handle elements together counter to a separation direction and which comprises at least one coupling element that is configured to establish, depending on a relative position of the handle elements, a form-fit connection of the handle elements counter to the separation direction. The at least one coupling element is embodied as a centering element for centering the form-fit connection.

9 Claims, 8 Drawing Sheets

Figures 1, 2:
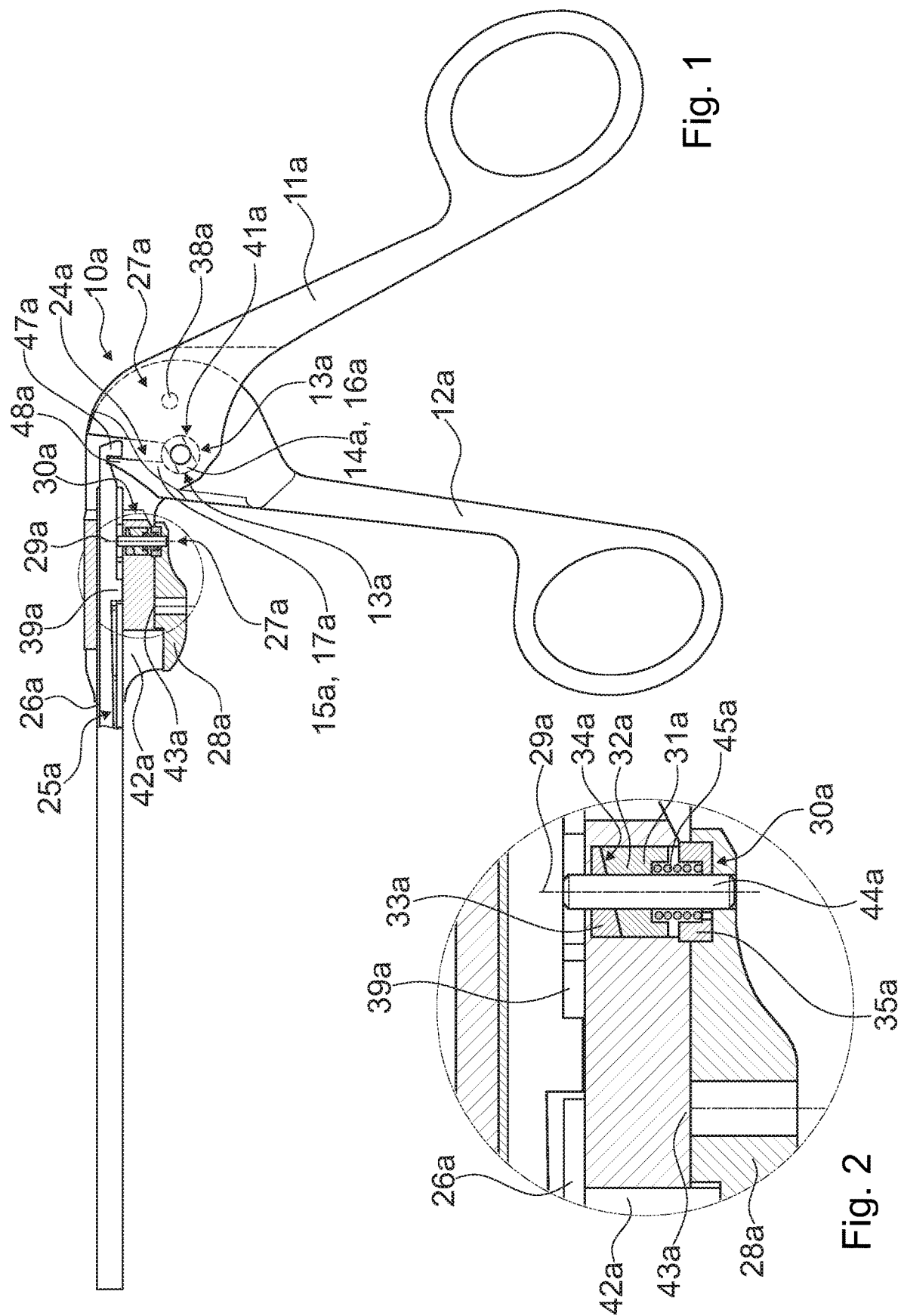

(51) Int. Cl.
*A61B 17/29* (2006.01)
*A61B 90/00* (2016.01)
*A61B 10/06* (2006.01)
*A61B 17/3205* (2006.01)

(52) U.S. Cl.
CPC ......... *A61B 10/06* (2013.01); *A61B 17/32053* (2013.01); *A61B 2017/2947* (2013.01); *A61B 2090/0813* (2016.02)

(56) References Cited

U.S. PATENT DOCUMENTS

| | | | |
|---|---|---|---|
| 9,005,239 B2* | 4/2015 | Seel | A61B 17/1611 606/208 |
| 2009/0209998 A1* | 8/2009 | Widmann | A61B 17/1611 606/207 |
| 2013/0253482 A1 | 9/2013 | Dannoritzer | |
| 2014/0236204 A1 | 8/2014 | Arit et al. | |

FOREIGN PATENT DOCUMENTS

| | | |
|---|---|---|
| DE | 102009060595 A1 | 6/2011 |
| DE | 202011052256 U1 | 1/2012 |
| DE | 102010044982 A1 | 3/2012 |
| WO | 0135838 A1 | 5/2001 |

OTHER PUBLICATIONS

International Search Report of the International Searching Authority dated Mar. 18, 2016 issued in corresponding International Application No. PCT/EP2015/075121.

International Preliminary Report on Patentability dated Jul. 25, 2017 issued in corresponding International Application No. PCT/EP2015/075121.

* cited by examiner

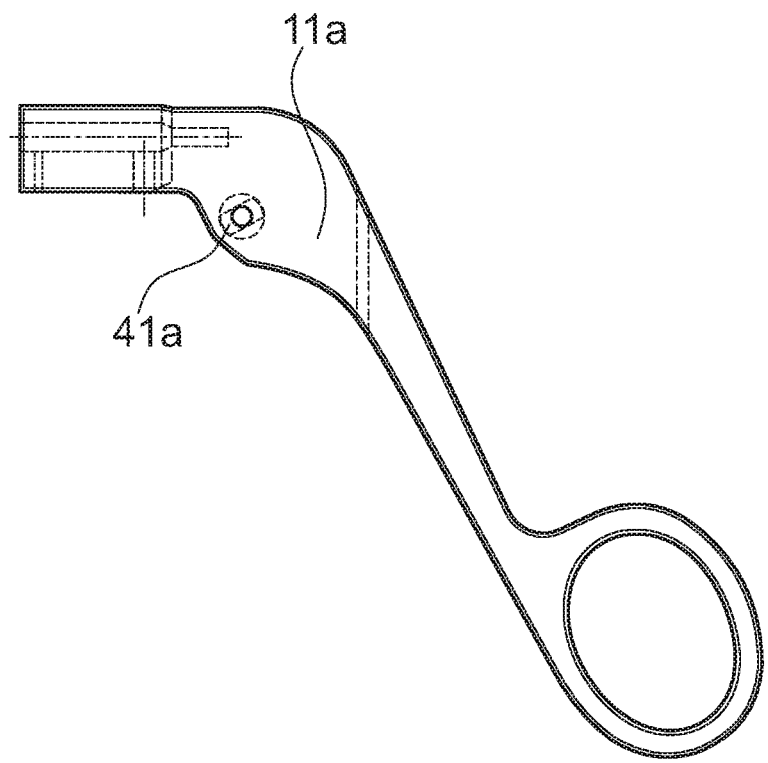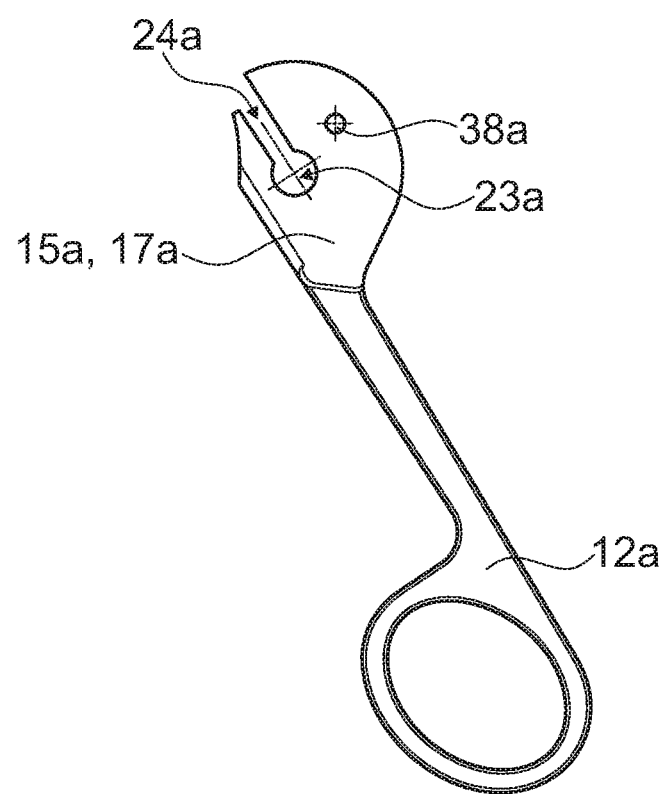
Fig. 4

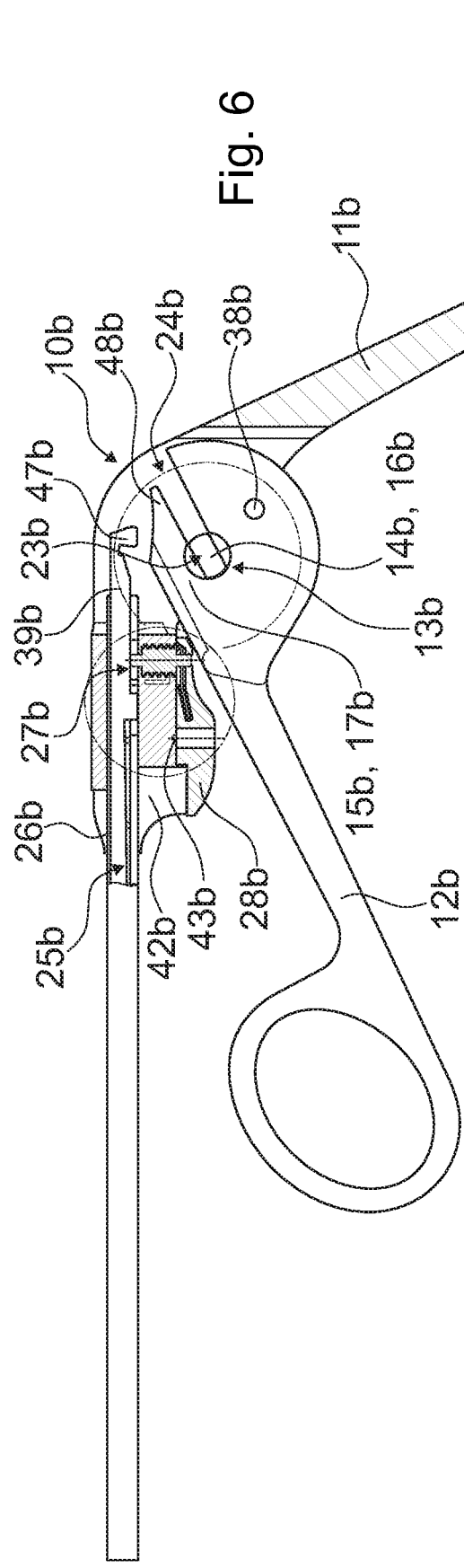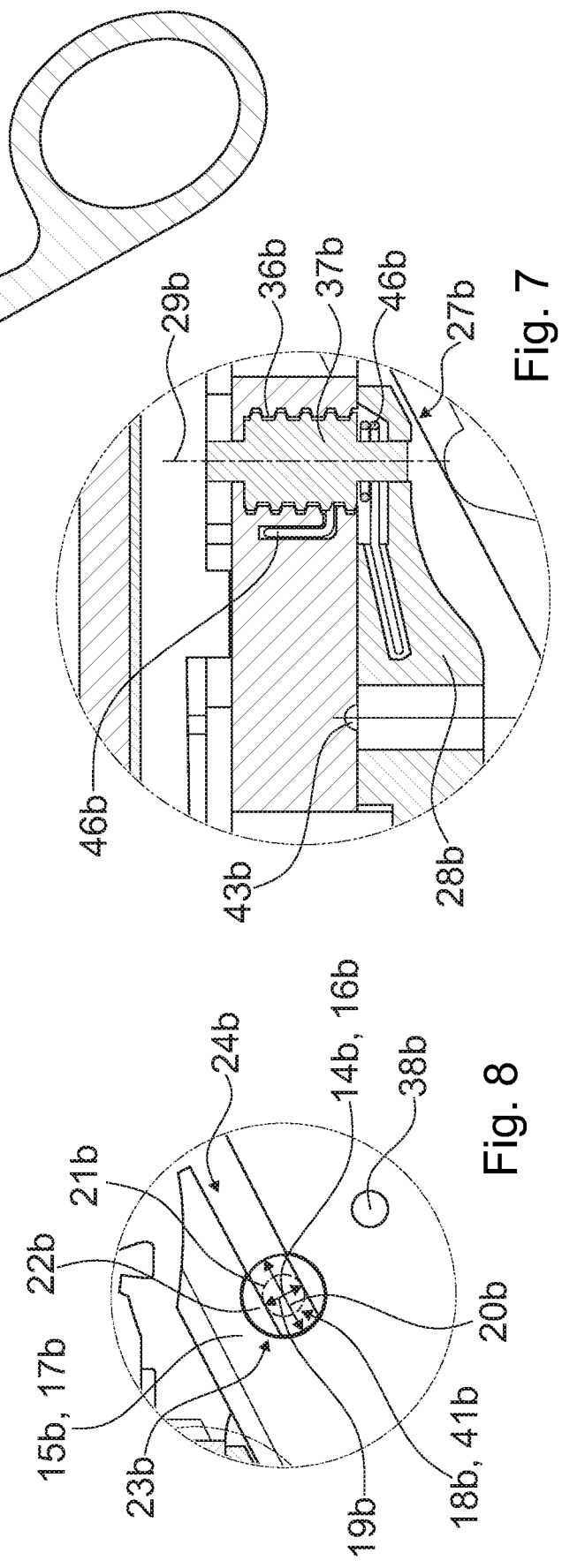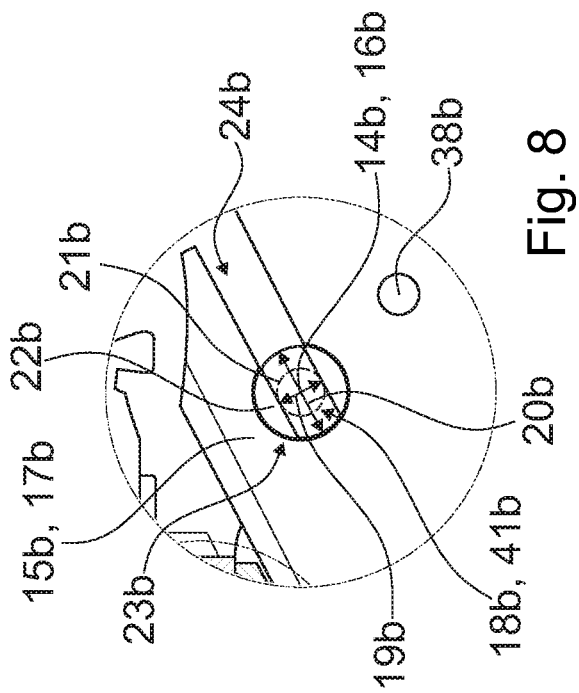

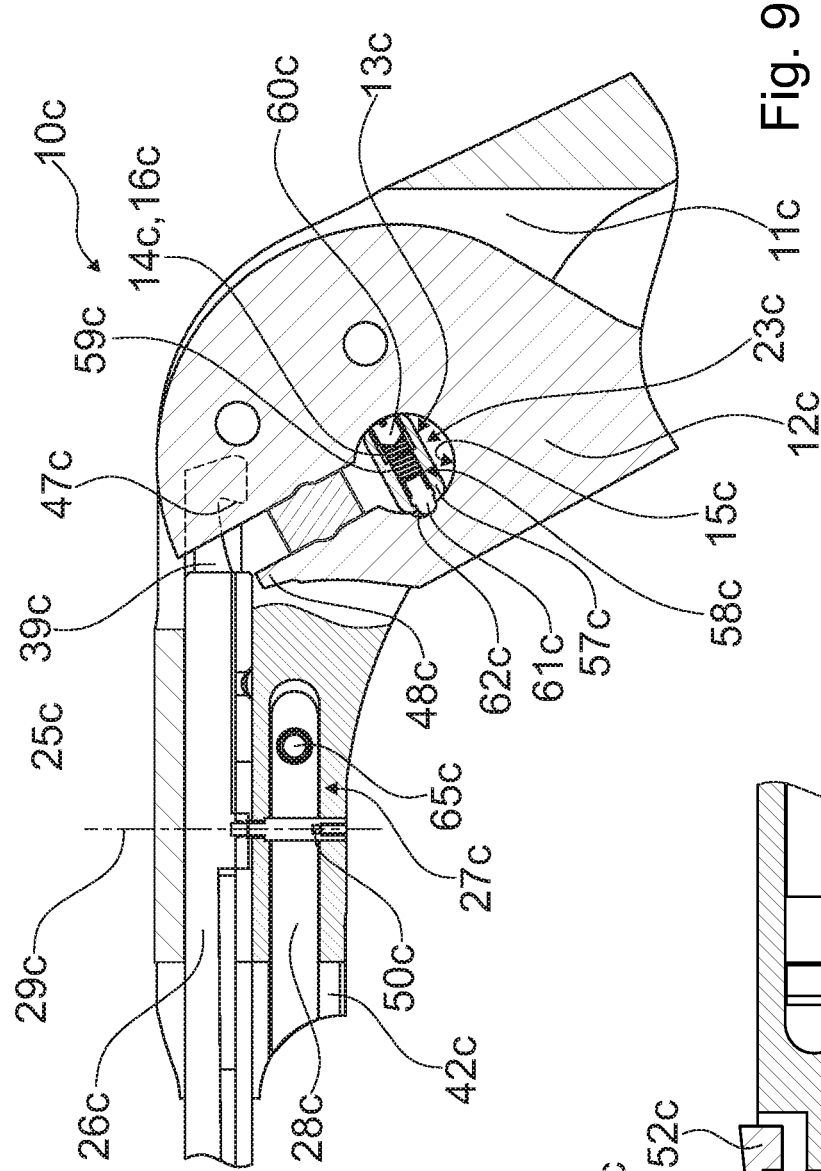
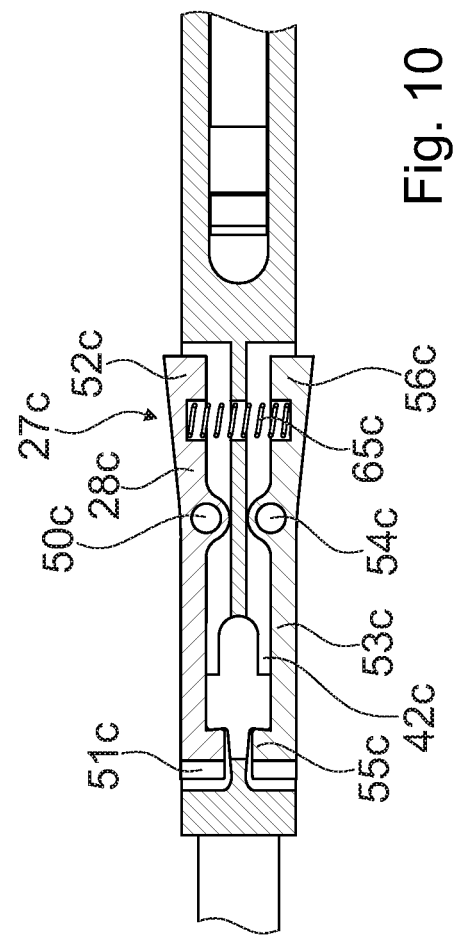

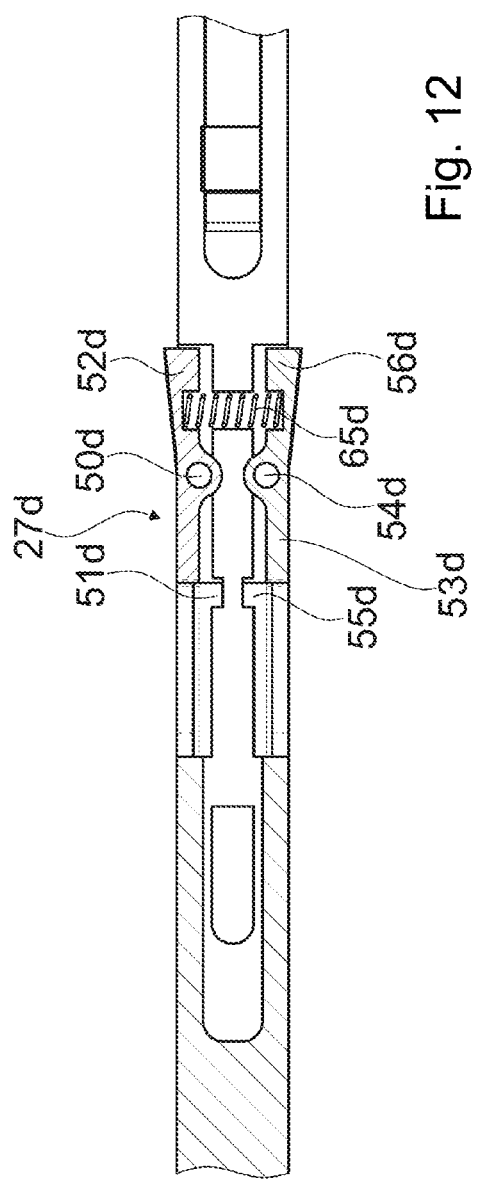

HANDLE DEVICE

CROSS REFERENCE TO RELATED APPLICATIONS

This application is a U.S. national stage application of PCT/EP2015/075121 filed on Oct. 29, 2015, which claims priority to German Patent Application No. DE 10 2015 100 945.5 filed on Jan. 22, 2015, the contents of which are incorporated herein by reference.

PRIOR ART

The invention relates to a handle device, in particular a surgical-tool handle device.

In DE 10 2008 058 207 A1 a handle device, in particular a surgical-tool handle device, has already been proposed, with a first and at least one second handle element and with a shear joint by means of which the two handle elements are pivotably connected, as well as with a coupling unit, which is configured to keep the two handle elements together, the coupling unit comprising at least one coupling element, which is configured to establish, depending on a relative position of the handle elements, a form-fit connection of the handle elements.

The objective of the invention is in particular to provide a generic device with improved characteristics regarding a simple construction. The objective is achieved, according to the invention, by the features of patent claim 1 while advantageous implementations and further developments of the invention will become apparent from the subclaims.

Advantages of the Invention

The invention is based on a handle device, in particular a surgical-tool handle device, with a first handle element and a second handle element, and with a shear joint by means of which the two handle elements are connected pivotably and separably, and with a coupling unit, which is configured to keep the two handle elements together counter to a separation direction and which comprises at least one coupling element that is configured to establish, depending on a relative position of the handle elements, a form-fit connection of the handle elements counter to the separation direction wherein the at least one coupling element is embodied as a centering element for centering the form-fit connection. It is proposed that the handle device comprises at least one corresponding coupling element, which delimits an at least partly circle-shaped recess for accommodating the coupling element, wherein the coupling element and the corresponding coupling element are configured for establishing the form-fit connection via a translational movement in a plane that is at least substantially parallel to a rotary plane of the shear joint. This allows reducing a number of structural components of the handle device. Furthermore, a simple guidance of a rotary motion of the handle elements is achievable when actuating the handle device in a shear grip. Beyond this, a handle device is achievable the structural components of which may be separated easily for separate cleaning. Furthermore a coupling element is achievable which is embodied in a structurally particularly simple fashion. Moreover a particularly simple movement for establishing the form-fit connection is achievable.

By a "shear joint" is in particular, in this context, a mechanical connection of the handle elements to be understood which allows a relative rotary motion of the two handle elements about a shared rotary axis that is located perpendicularly to a plane spanned by the two handle elements and within their connection. "Configured" is in particular to mean specifically programmed, designed and/or equipped. By an object being configured for a certain function is to be understood, in this context, that the object fulfills and/or implements said certain function in at least one application state and/or operating state. By the two handle elements being "connected separably" by means of the shear joint is to be understood, in this context, that the two handle elements are separable from each other by a reversal of a mounting movement. A "separation direction" is to mean, in this context, a direction along which a separation of the two handle elements is intended. By "the coupling unit being configured to hold the two handle elements together counter to a separation direction" is to be understood, in this context, that the coupling unit holds the two handle elements together in such a way that said handle elements are separable from each other only in a certain angular position relative to each other along the separation direction and, in a mounted state, movements of the handle elements counter to the separation direction are blocked by the coupling unit. In particular, the coupling element is fixedly mounted, in particular plugged, on one of the handle elements. Principally the coupling element may be arranged on the one handle element in a one-part implementation, e.g. by welding, or the coupling element may be embodied as a molding of one of the handle elements.

The term "an at least partly circle-shaped recess" is to mean, in this context, a recess having a partial region which is delimited by a circle-shaped contour that is open along no more than a third, preferably along no more than a sixth, of a circle circumference wherein, at an opening of the circle-shaped contour, there are further partial regions of the recess directly subsequent to the partial region that is delimited by the circle-shaped contour. By the translational movement extending "in a plane that is at least substantially parallel to a rotary plane of the shear joint" is to be understood, in this context, that a direction in which the translational movement extends includes with a plane that is parallel to the rotary plane of the shear joint an angle of maximally five degrees, preferably of maximally three degrees and especially preferentially of maximally one degree. The translational movement may in particular extend completely within the plane that is parallel to the rotary plane of the shear joint.

In a further development of the invention it is proposed that the at least one coupling element comprises at least one region having, in a first transverse direction, a first extension and having, in a second transverse direction, a second extension which is greater than the first extension. In this way, a separation direction can be indicated in a structurally simple manner. Furthermore a blockage of a pull-off movement is achievable in a direction extending at least partly perpendicularly to an intended separation direction. In this context, a "transverse direction" is to be understood as a direction extending, in a mounted state of the coupling element, in a plane that is perpendicular to a rotary axis of the shear joint. In particular, the transverse directions extend perpendicularly with respect to a mounting direction of the coupling element on one of the handle elements. By a "first transverse direction" and a "second transverse direction" are in this context transverse directions to be understood which extend perpendicularly to each other. In particular, the two handle elements are mounted via a movement extending perpendicularly to the first transverse direction.

It is also proposed that the at least one coupling element is implemented in such a way that it is rounded off at ends of the region. This allows achieving a simple mounting movement as well as avoiding canting of the coupling element with one of the handle elements during assembly.

It is moreover proposed that the corresponding coupling element delimits a guiding channel for guiding the coupling element into the at least partly circle-shaped recess. In this way a guiding element for guiding the coupling element may be rendered available in a structurally simple fashion. Furthermore, this allows achieving intuitive guiding of the mounting movement when the handle device is assembled.

It is also proposed that the corresponding coupling element forms a further centering element. This allows reducing a number of structural components of the handle device. Furthermore, a particularly simple centering of the shear joint is achievable.

Furthermore it is proposed that the coupling element and the corresponding coupling element comprise at least one locking unit, which is configured for locking the handle elements in at least one locking position. In this way the handle elements may be secured in a position which allows fault-free assembly of the handle elements in a position in which the tool is mountable in a fault-free manner.

The invention is moreover based on a handle device according to the preamble of claim 1 and in particular to one of the preceding claims. It is proposed that the handle device comprises a tool unit as well as a securing unit featuring a locking lever which has a pivot axis for pivoting between a release position and a fixation position for the tool unit, the securing unit being configured for reversibly holding the tool unit on at least one of the handle elements. This allows achieving demounting of the tool unit, e.g. for cleaning purposes, separately from the handle elements. Furthermore, tool-less demounting of the tool unit is achievable. By a "tool unit" is to be understood, in this context, a unit which is configured to be held in at least one of the handle elements and which is at least configured for holding the tool and is configured at least for holding a tool or is embodied in a one-part implementation with the tool. In particular, the tool unit comprises structural components for an actuation of the tool. By a "locking lever" is to be understood, in this context, a unit which is supported pivotably and which supports at least the tool unit and, if applicable, further structural components of the handle device at least in a fixed position. In particular, the tool unit and, if applicable, further structural components of the handle device is/are released by pivoting the locking lever to allow them to be at least cleaned and preferably to be demounted. In particular, via the pivoting between the fixation position and the release position a movement is initiated which is effected at least partly, preferably completely along an extension direction of the pivot axis.

It is further proposed that the securing unit comprises a cam mechanism with two inclined planes sliding on one another, which slide off one another to release the tool unit when the locking lever is pivoted into the release position. In this way a simple construction of the securing unit is achievable.

Furthermore it is proposed that the securing unit comprises a thread and a thread screw which is screwed out of the thread and releases the tool unit when the locking lever is pivoted. This allows achieving a securing unit implemented in a structurally especially simple fashion.

It is moreover proposed that the tool unit comprises a shaft for accommodating a tool, and a stop on which the shaft is supported, and that the locking lever is configured to directly fixate the stop on one of the handle elements in the fixation position and to release the stop in the release position. This allows achieving a securing unit implemented in a structurally especially simple fashion.

Beyond this it is proposed that the tool unit comprises at least one upper attachment, which forms a tool together with the first handle element and which is in the fixation position fixated to the first handle element by the locking lever. This allows achieving a securing unit implemented in a structurally especially simple fashion.

It is also proposed that the securing unit comprises another locking lever. This allows achieving a securing unit featuring increased reliability.

Moreover a system is proposed, with a handle device according to one of the preceding claims, and with a tool, in particular a surgical tool.

DRAWINGS

Further advantages may be gathered from the following description of the drawings. The drawings show four exemplary embodiments of the invention. The drawings, the description and the claims contain a plurality of features in combination. Someone skilled in the art will purposefully also consider the features separately and will find further expedient combinations.

Figure 3:
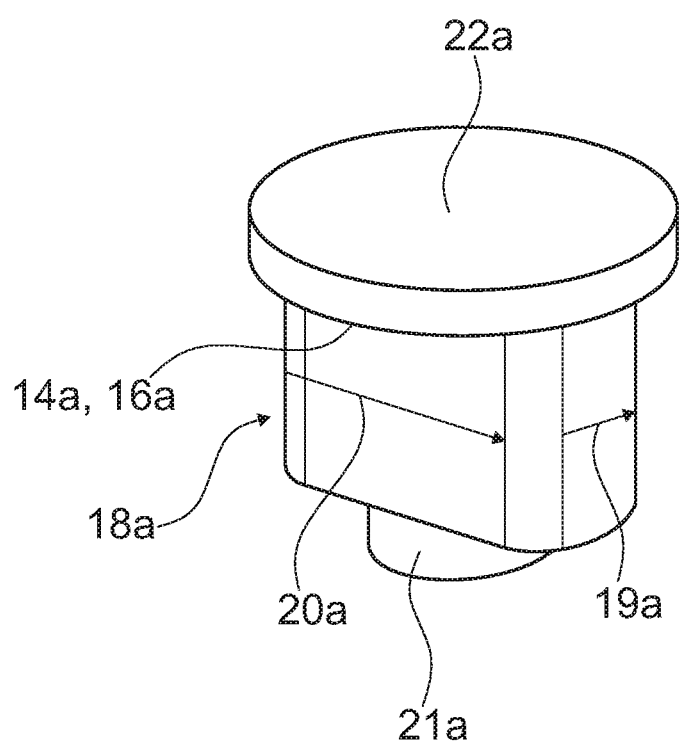
Figure 5:
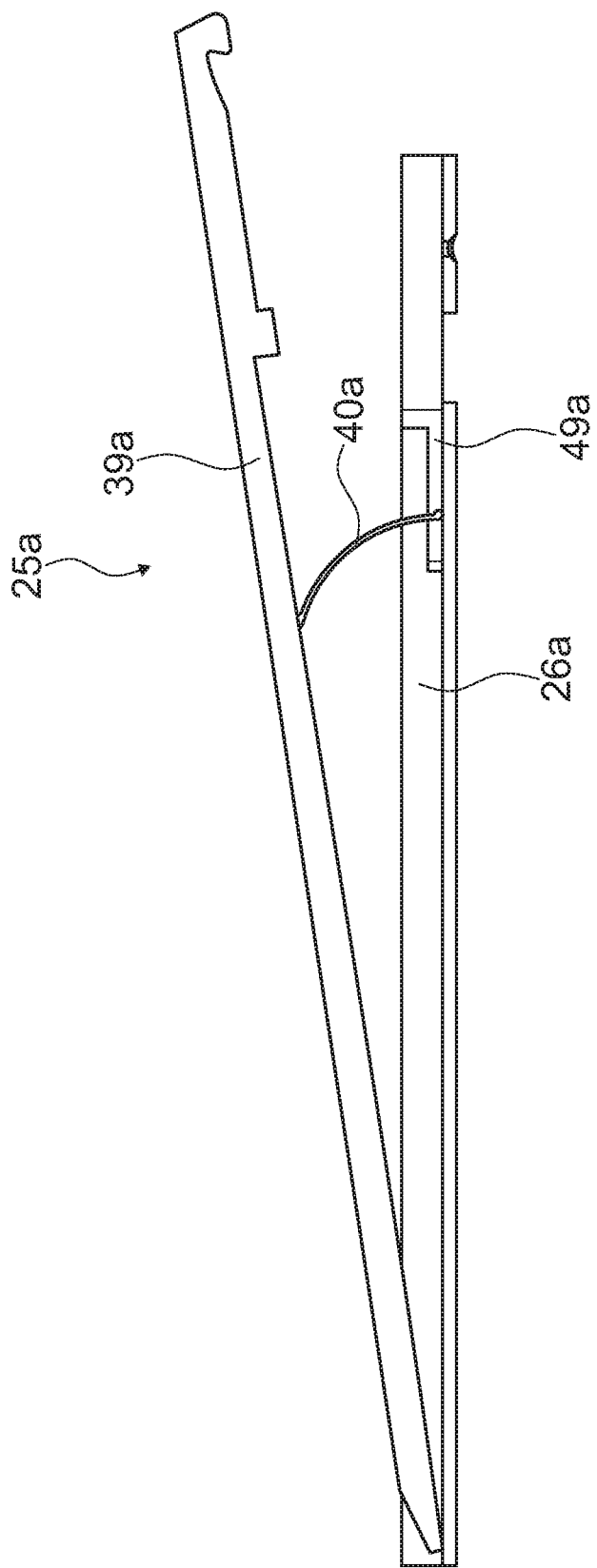
Figure 11:
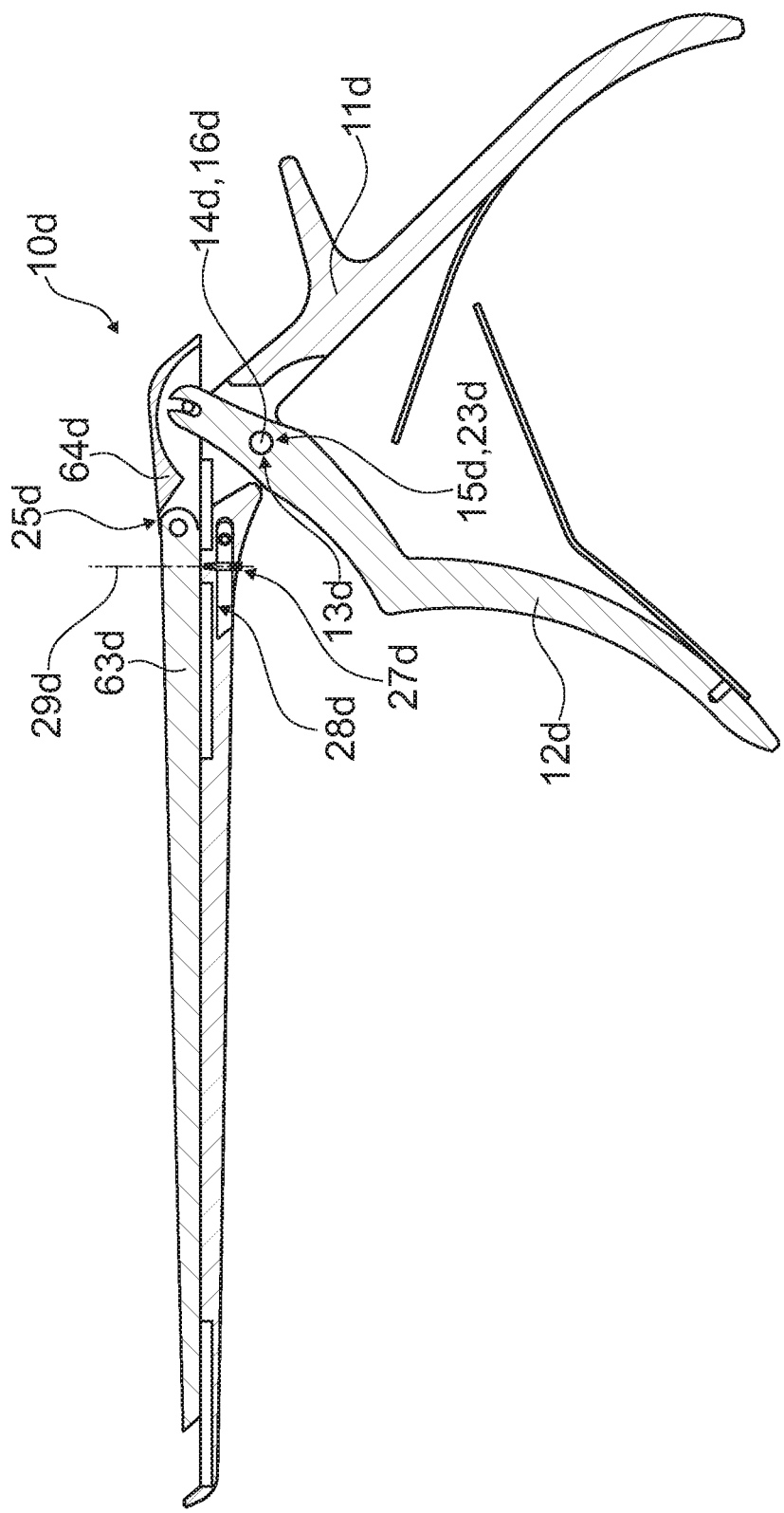

It is shown in:

FIG. 1 a handle device according to a first exemplary embodiment of the invention, FIG. 2 a detailed presentation of a section of the handle device of the first exemplary embodiment, with a securing unit comprising a locking lever, FIG. 3 a detailed presentation of a coupling element of the handle device, FIG. 4 a detailed presentation of a first handle element and a second handle element, FIG. 5 a detailed presentation of a tool unit of the handle device, with a slider, with a mobile holding element that is fixedly connected to the slider, and with a shaft in which the slider is supported and which comprises a groove for guiding the holding element, FIG. 6 a handle device according to a second exemplary embodiment of the invention, FIG. 7 a detailed presentation of a section of the handle device of the second exemplary embodiment, with a securing unit comprising a locking lever, and FIG. 8 a detailed presentation of the regions of a first handle element and a second handle element, with a coupling element and a corresponding coupling element, FIG. 9 a detailed presentation of a third exemplary embodiment, with two locking levers, FIG. 10 a sectional view of the two locking levers of the third exemplary embodiment, FIG. 11 a schematic presentation of a fourth exemplary embodiment of the invention, with two locking levers, and FIG. 12 a sectional view of the two locking levers of the fourth exemplary embodiment.

DESCRIPTION OF THE EXEMPLARY EMBODIMENTS

FIGS. 1 and 2 show a handle device 10a, which is embodied as a surgical-tool handle device, with a first handle element 11a and a second handle element 12a, and with a shear joint by means of which the two handle elements 11a, 12a are connected pivotably and separably, and with a coupling unit 13a, which is configured to keep the two handle elements 11a, 12a together counter to a separation direction and which comprises a coupling element 14a that is configured to establish, depending on a relative position of the handle elements 11a, 12a, a form-fit connection of the handle elements 11a, 12a counter to the separation direction. The first handle element 11a is embodied as a main part of the handle device 10a and is configured for accommodating a tool. The second handle element 12a is configured to be stuck upon the first handle element 11a at the coupling unit 13a. The first handle element 11a and the second handle element 12a are made of steel.

The coupling element 14a is implemented as a centering element 16a for centering the form-fit connection. The centering element 16a may be referred to herein as a coupler. On actuation of the handle device 10a, the second handle element 12a is rotated with respect to the first handle element 11a, wherein a rotation is effected about a rotary axis of the shear joint, which rotary axis extends centrally through the coupling element 14a which is embodied as a centering element 16a. The second handle element 12a is guided in its movement by the coupling element 14a which is embodied as a centering element 16a, wherein the coupling element 14a which is embodied as a centering element 16a contacts the second handle element 12a and blocks a movement of the second handle element 12a in a direction that is perpendicular to the rotary axis of the shear joint, with the exception of a movement in the separation direction.

The coupling element 14a comprises a region 18a which has, in a first transverse direction 19a, a first extension and, in a second transverse direction 20a, a second extension which is greater than the first extension (FIG. 3). The second extension amounts to 1.9 times the first extension. The coupling element 14a is implemented in such a way that it is rounded off at ends of the region 18a in a plane in which the transverse directions 19a, 20a extend. A rounding off of the ends of the region 18a is implemented as a two-step abrasion. In alternative implementations the coupling element 14a may be embodied in such a way that it is completely rounded off by abrasion or is rounded off in a plurality of steps at ends of the region 18a.

In a direction that is perpendicular to the first transverse direction 19a and the second transverse direction 20a, the coupling element 14a comprises at an end piece a head 22a protruding over the region 18a and having a circle-shaped cross-section. The head 22a blocks a lift-off movement of the first handle element 11a and the second handle element 12a from one another along the rotary axis of the shear joint. At an end piece of the coupling element 14a that faces away from the head 22a, the coupling element 14a comprises a plug-in pin 21a, which is configured to be stuck into a corresponding bore of the first handle element 11a. When plugged into the corresponding bore, the plug-in pin 21a is welded to the first handle element 11a. The bore is implemented in a center of a rectangular countersink 41a of the first handle element 11a. The rectangular countersink 41a corresponds in its outer dimensions to a cross-section of the region 18a of the coupling element 14a, with the transverse directions 19a, 20a. The coupling element 14a is inserted into the rectangular countersink 41a and the bore with the region 18a and the plug-in pin 21a and is in the inserted state partly sunk in the rectangular countersink 41a but protrudes over a surface of the first handle element 11a in surroundings of the rectangular countersink 41a. A position and an orientation of the coupling element 14a on the first handle element 11a, in the mounted state, are unambiguously determined by the rectangular countersink 41a and the bore.

The handle device 10a comprises a corresponding coupling element 15a, which delimits a partly circle-shaped recess 23a for receiving the coupling element 14a. The corresponding coupling element 15a is embodied as a partial region of the second handle element 12a, which has the partly circle-shaped recess 23a. The partly circle-shaped recess 23a comprises a partial region which is delimited by a circle-shaped contour that is opened along a sixth of a circle circumference. A diameter of the partial region which is delimited by the circle-shaped contour is equivalent to the second extension of the region 18a of the coupling element 14a in the second transverse direction 20a.

The corresponding coupling element 15a delimits a guiding channel 24a for guiding the coupling element 14a into the partly circle-shaped recess 23a. At an opening point of the circle circumference of the circle-shaped contour in the second handle element 12a, the guiding channel 24a opens into the partial region of the partly circle-shaped recess 23a that is delimited by the open circle-shaped contour. The guiding channel 24 a may optionally be closed by inserting a closure element which is removable or is fixedly connected to the second handle element 12a. A width of the guiding channel 24a is equivalent to the first extension of the region 18a of the coupling element 14a in the first transverse direction 19a. The second handle element 12a comprises, in addition to the partly circle-shaped recess 23a, an opening 38a implemented as a bore, which is configured for inserting a teflon element avoiding a direct friction of the first handle element 11a and the second handle element 12a on one another.

The corresponding coupling element 15a forms a further centering element 17a. The coupling element 14a, which is embodied as a centering element 16a, and the corresponding coupling element, which is embodied as a centering element 17a, constitute the only elements of the handle device 10a which establish the form-fit connection. During a rotation of the shear joint, the further centering element 17a carries out a rotation about the centering element 16a. A translational displacement of the second handle element 12a away from the rotary axis of the shear joint is blocked by the diameter of the partial region of the partly circle-shaped recess 23a, which is adapted to the second extension of the region 18a of the coupling element 14a in the second transverse direction 20a and is delimited by the circle-shaped contour.

The coupling element 14a and the corresponding coupling element 15a are configured for establishing the form-fit connection via a translational movement in a plane that is parallel to a rotary plane of the shear joint. In one end of the guiding channel 24a, which faces away from the partial region of the partly circle-shaped recess 23a that is delimited by the open circle-shaped contour, the second handle element 12a is applied to a rounded end of the region 18a of the coupling element 14a for the purpose of mounting the handle elements 11a, 12a of the handle device 10a. Via a translational movement extending along the second transverse direction 20a, which extends completely within the plane that is situated parallel to the rotary plane of the shear joint, the second handle element 12a is slid onto the coupling element 14a until the coupling element 14a is completely accommodated within the partial region of the partly circle-shaped recess 23a that is delimited by the circle-shaped contour. In this position the second handle element 12s is pivotable about the coupling element 14a. Principally, the coupling element 14a and the corresponding coupling element 15a may be configured for establishing the form-fit connection via a translational movement in a plane that is substantially parallel to the rotary plane of the shear joint and is, for example, inclined with respect to the rotary plane of the shear joint towards the first handle element 11a by three degrees, as a result of which the second handle element 12a engages underneath the coupling element 14a during assembly.

The handle device 10a comprises a tool unit 25a for holding a tool, and comprises a securing unit 27a featuring a locking lever 28a which has a pivot axis 29a for pivoting between a release position and a fixation position for the tool unit 25a, the securing unit 27a being configured for reversibly holding the tool unit 25a on at least one of the handle elements 11a, 12a. Principally, the handle device 10a may as well comprise a tool unit 25a which is fixedly supported on the first handle element 11a, wherein a securing unit 27a featuring a locking lever 28a is dispensed with and the tool is secured, for example, by means of a screw. It is also principally conceivable that the handle device 10a comprises a tool unit 25a for holding a tool and comprises a securing unit 27a featuring a locking lever 28a while comprising a first handle element 11a and a second handle element 12a which are connected fixedly and inseparably in a shear joint by means of a screw or a rivet.

The locking lever 28a is embodied as a metal plate component and is supported on the first handle element 11a by means of a compression spring button 43a. The tool unit 25a comprises a slider 39a featuring a hook 47a that is to be actuated via the second handle element 12a, and comprises a shaft 26a which is implemented as an open tube and supports the slider 39a. A stop 42a is welded to the shaft 26a and prevents the tool unit 25a from being pulled too far into the first handle element 11a.

The securing unit 27a comprises a cam mechanism 30a with two inclined surfaces 32a, 34a sliding on one another which, for releasing the tool unit 25a, slide off one another when the locking lever 28a is pivoted into the release position. The cam mechanism 30a comprises a pin 44a configured for holding the tool unit 25a, a first ring 31a featuring a first inclined surface 32a, a second ring 33a featuring a second inclined surface 34a, a compression spring 45a for resetting the first ring 31a and a fixation ring 35a. The pivot axis 29a is equivalent to a middle axis of the pin 44a. The rings 31a, 33a each have, on a side at which the respective inclined surfaces 32a, 34a are implemented, a height varying along the circle circumference. The inclined surfaces 32a, 34a of the rings 31a, 33a are implemented in such a way that they correspond to each other. In the fixation position the rings 31a, 33a are supported contacting each other with their inclined surfaces 32a, 34a in such a way that a maximum-height partial area of the first ring 31a is adjacent on a minimum-height partial area of the second ring 33a and the two rings 31a, 33a complement each other together forming a whole ring having a constant height. In the fixation position the pin 44a pushes against the slider 39a, and thus fixedly holds the tool unit 25a.

The fixation ring 35a is fixated on the first handle element 11a via welding. Between the fixation ring 35a and the first ring 31a, the compression spring 45a is arranged. The compression spring 45a is configured to secure the pin 44a against inadvertent pulling out and to press the first ring 31a against the second ring 33a in the fixation position. The first ring 31a is fixedly connected to the pin 44a, as a result of which it is also turned when the pin 44a is turned. The second ring 33a is fixedly connected to the first handle element 11a.

When the locking lever 28a is pivoted into the release position, the locking lever is pivoted about the pivot axis 29a, as a result of which the pin 44a and the first ring 31a rotate about the pivot axis 29a. Due to this, the first ring 31a is rotated with respect to the stationary second ring 33a. The inclined surfaces 32a, 34a thus slide off one another and the first ring 31a is pushed away from the second ring 33a. The rings 31a, 33a continue to be in contact via their inclined surfaces 32a, 34a, and a distance between the sides of the rings 31a, 33a facing away from the inclined surfaces 32a, 34a is increased. The pin 44a is also pushed away from the second ring 33a together with the first ring 31a, and the slider 39a of the tool unit 25a is released. In the release position the first ring 31a is spaced apart from the second ring 33a and the slider 39a of the tool unit 25a is released, as a result of which the tool unit 25a may now be demounted.

For the purpose of laying a tool into the handle device 10a, the shear joint is opened and then the tool unit 25a is inserted into the first handle element 11a until the hook 47a of the slider 39a engages behind the second handle element 12a and a projection 48a of the second handle element 12a latches into the hook 47a.

The tool unit 25a for holding a tool comprises a mobile holding element 40a, which is fixedly connected to the slider 39a and comprises the shaft 26a, in which the slider 39a is supported and which comprises a groove 49a for guiding the holding element 40a. The holding element 40a is embodied as a leaf spring and is welded with the slider 39a. The slider 39a is translationally displaceable, with respect to the shaft 26a, in the groove 49a via the guidance of the holding element 40a which is embodied as a leaf spring, but is held on the shaft 26a by the holding element 40a which is embodied as a leaf spring, as a result of which it is not possible to completely remove the slider 39a from the shaft 26a. For cleaning purposes the shaft 26a and the slider 39a are removable out of the first handle element 11a. Following removal of the shaft 26a and the slider 39a from the first handle element 11a, the shaft 26a and the slider 39a may be partly separated from each other and cleaned, wherein the slider 39a remains connected to the shaft 26a via the holding element 40a which is embodied as a leaf spring. In an alternative implementation it is conceivable, for example, that the holding element 40a which is embodied as a leaf spring is fixated to the slider 39a via a securing screw.

In FIGS. 6 to 12 three further exemplary embodiments of the invention are shown. The following descriptions and the drawings are substantially restricted to the differences between the exemplary embodiments, wherein regarding structural components having the same denomination, in particular regarding structural components with the same reference numerals, principally the drawings and/or the description of the other exemplary embodiments, in particular of FIGS. 1 to 5, may be referred to. For distinguishing between the exemplary embodiments, the letter a is added to the reference numerals of the exemplary embodiment in FIGS. 1 to 5. In the exemplary embodiments of FIGS. 6 to 12 the letter a has been substituted by the letters b to d.

FIGS. 6 to 8 show a handle device 10b implemented as a surgical-tool handle device, with a first handle element 11b and a second handle element 12b, and with a shear joint by means of which the two handle elements 11b, 12b are pivotably and separably connected, and with a coupling unit 13b, which is configured to keep the two handle elements 11b, 12b together counter to a separation direction and comprises a coupling element 14b configured to establish, depending on a relative position of the handle elements 11b, 12b, a form-fit connection of the handle elements 11b, 12b counter to the separation direction. The coupling element 14b is embodied as a centering element 16b for centering the form-fit connection. The coupling element 14b and a corresponding coupling element 15b of the coupling unit 13b, which delimits an at least partly circle-shaped recess 23b for accommodating the coupling element 14b, are embodied identically to the preceding exemplary embodiment.

The handle device 10b comprises a tool unit 25b for holding a tool and comprises a securing unit 27b, featuring a locking lever 28b which has a pivot axis 29b for pivoting between a release position and a fixation position for the tool unit 25b, the securing unit 27b being configured for reversibly holding the tool unit 25b on at least one of the handle elements 11b, 12b. The locking lever 28b is configured as a metal plate component and is supported on the first handle element 11b via a compression spring button 43b. The tool unit 25b comprises a slider 39b featuring a hook 47b, which is to be actuated via the second handle element 12b, and comprises a shaft 26b embodied as an open tube and supporting the slider 39b. A stop 42b is welded to the shaft 26b and prevents the tool unit 25b from being pulled too far into the first handle element 11b.

The securing unit 27b comprises a thread 36b and a thread screw 37b which is screwed out of the thread 36b and releases the tool unit 25b when the locking lever 28b is pivoted. The thread 36b is implemented in the first handle element 11b. The thread 36b and the thread screw 37b are embodied as trapezoidal threads. In the fixation position the thread screw 37b is completely accommodated in the thread 36b and pushes against the slider 39b with an end projection, thus holding the tool unit 25b. A second end projection is fixedly connected to the locking lever 28b. The pivot axis 29b extends centrally through the thread screw 37b. When the locking lever 28b is pivoted, the thread screw 37b is turned and rotates out of the thread 36b by a quarter-turn, as a result of which the end projection is removed from the slider 39b and the tool unit 25b is released.

A torsion spring 46b is accommodated in a countersunk receptacle, which extends around the thread 36b and is implemented in the first handle element 11b and the locking lever 28b. The torsion spring 46b contacts the thread screw 37b. When the locking lever 28b is pivoted about the pivot axis 29b, the torsion spring 46b is tensioned by the turning thread screw 37b. When the locking lever 28b is pivoted back into the fixation position, the torsion spring 46b exerts a pressure onto the thread screw 37b and screws the thread screw 37b completely back into the thread 36b.

FIGS. 9 and 10 show a section of a handle device 10c implemented as a surgical-tool handle device, with a first handle element 11c and a second handle element 12c, and with a shear joint by means of which the two handle elements 11c, 12c are connected pivotably and separably, and with a coupling unit 13c configured to keep the two handle elements 11c, 12c together counter to a separation direction and comprising a coupling element 14c, which is configured to establish, depending on a relative position of the handle elements 11c, 12c, a form-fit connection of the handle elements 11c, 12c counter to the separation direction. The coupling element 14c is embodied as a centering element 16c for centering the form-fit connection. The handle device 10c comprises a corresponding coupling element 15c of the coupling unit 13c, which delimits a partly circle-shaped recess 23c for receiving the coupling element 14c. The corresponding coupling element 15c is implemented as a partial region of the second handle element 12c featuring the partly circle-shaped recess 23c.

The handle device 10c comprises a tool unit 25c for holding a tool, and comprises a securing unit 27c featuring a locking lever 28c which has a pivot axis 29c for pivoting between a release position and a fixation position for the tool unit 25c, the securing unit 27c being configured for reversibly holding the tool unit 25c on at least one of the handle elements 11c, 12c. The locking lever 28c is embodied as a metal plate component. The tool unit 25c comprises a slider 39c featuring a hook 47c which is to be actuated via the second handle element 12c, and comprises a shaft 26c embodied as an open tube and supporting the slider 39c. The second handle element 12c comprises a projection 48c, which is configured for latching into the hook 47c of the slider 39c and for coupling the slider 39c and the second handle element 12c. Furthermore the shaft 26c is configured for accommodating the tool. The handle device 10c comprises a stop 42c which is removably fixated to the first handle element 11c and is configured to prevent the tool unit 25c from being pulled too far into the first handle element 11c.

The locking lever 28c fixates the stop 42c directly on the first handle element 11c in the fixation position. The locking lever 28c is fixated to the first handle element 11c by means of a locking bolt 50c. In the release position the locking lever 28c is configured for releasing the shaft 26c. The locking lever 28c is pivotable about an axis of the locking bolt 50c. The locking lever 28c comprises a projecting edge 51c which, in the fixation position, acts onto a front side of the stop 42c and secures the stop 42c against the first handle element 11c (FIG. 10). The locking lever 28c comprises an actuating region 52c, which faces away from the projecting edge 51c. By means of a pressure onto the actuating region 52c of the locking lever 28c, the locking lever 28c is pivoted about the locking bolt 50c and the projecting edge 51c is lifted off the stop 42c, as a result of which the stop 42c may be demounted. Following demounting of the stop 42c, it is possible to demount the shaft 26c and further components of the tool unit 25c.

The securing unit 27c of the handle device 10c features a further locking lever 53c, which is arranged on a side of the first handle element 11c that faces away from the locking lever 28c and which fixates the stop 42c directly on the first handle element 11c in the fixation position (FIG. 10). A locking bolt 54c secures the further locking lever 53c on the first handle element 11c. The further locking lever 53c is implemented identically to the first locking lever 28c, also comprising a projecting edge 55c and an actuating region 56c. By a pressure onto the actuating region 56c, the further locking lever 53c is pivoted about the locking bolt 54c and releases the stop 42c. For the purpose of demounting the tool unit 25c, by bilateral pressure on the handle device 10c the actuating regions 52c, 56c are actuated and the locking levers 28c, 53c are pivoted about the locking bolts 50c, 54c into the release positions to allow demounting the stop 42c and further components of the tool unit 25c. For complete disassembly of the handle device 10c the handle elements 11c, 12c may then be separated from each other. The securing unit 27c comprises a spring 65c, which is arranged between the two locking levers 28c, 53c and acts onto the actuating regions 52c, 56c. The spring 65c secures the locking levers 28c, 53c in the fixation position.

The coupling element 14c and the corresponding coupling element 15c comprise a locking unit 57c, which is configured to lock the handle elements 11c, 12c in a locking position (FIG. 10). In the locking position it is ensured that the projection 48c of the second handle element 12c can engage into the hook 47c of the slider 39c, thus allowing a successful coupling of the slider 39c to the second handle element 12c. The locking unit 57c comprises a pressure piece 58c implemented of a compression spring 59c, a thread pin 60c and ball pin 61c having a hemisphere-shaped head with a diameter of 1.2 cm. The compression spring 59c is implemented as a helical spring with a length of 4 cm, an outer diameter of 1.5 cm and an inner diameter of 1.1 cm. The pressure piece 58c is accommodated in the coupling element 14c. The locking unit 57c comprises a hemisphere-shaped recess 62c on the corresponding coupling element 15c, which is configured for accommodating the hemisphere-shaped head of the ball pin 61c.

In FIGS. 11 and 12 a further exemplary embodiment of a handle device 10d is shown, which is embodied as a surgical-tool handle device. The handle device 10d is implemented as a Kerrison punch by means of which, for example, human tissue, e.g. spinal marrow, can be punched out. The handle device 10d comprises a first handle element 11d and a second handle element 12d, and comprises a shear joint by means of which the two handle elements 11d, 12d are connected pivotably and separably. The handle device 10d further comprises a coupling unit 13d, which is configured to keep the two handle elements 11d, 12d together counter to a separation direction and comprises a coupling element 14d, which is configured to establish, depending on a relative position of the handle elements 11d, 12d, a form-fit connection of the handle elements 11d, 12d counter to the separation direction. The coupling element 14d is embodied as a centering element 16d for centering the form-fit connection. The handle device 10d comprises a corresponding coupling element 15d of the coupling unit 13d, which delimits a partly circle-shaped recess 23d for receiving the coupling element 14d. The corresponding coupling element 15d is implemented as a partial region of the second handle element 12d, which comprises the partly circle-shaped recess 23d.

The handle device 10d comprises a tool unit 25d for holding a tool and comprises a securing unit 27d featuring a locking lever 28d which has a pivot axis 29d for pivoting between a release position and a fixation position for the tool unit 25d, the securing unit 27d being configured for reversibly holding the tool unit 25d on at least one of the handle elements 11d, 12d. The locking lever 28d is embodied as a metal plate component. The tool unit 25d comprises two upper attachments 63d, 64d, which form a tool together with the first handle element 11d. The first upper attachment 63d is arranged to the front of the second upper attachment 64d with respect to a punched edge of the tool. In a punching-out procedure human tissue is gripped between the first upper attachment 63d and the first handle element 11d and is punched out. The second upper attachment 64d is offset with respect to the first upper attachment 63d towards an operator of the handle device 10d.

The locking lever 28d is fixated to the first handle element 11d by means of a locking bolt 50d. In the fixation position the locking lever 28d fixates the first upper attachment 63d directly to the first handle element 11d. In the release position the locking lever 28d is configured for releasing the first upper attachment 63d. The locking lever 28d is pivotable about an axis of the locking bolt 50d. The locking lever 28d comprises a projecting edge 51d, which in the fixation position engages into the first upper attachment 63d and secures the first upper attachment 63d on the first handle element 11d. On a side facing away from the projecting edge 51d, the locking lever 28d comprises an actuating region 52d, which protrudes from a plane of the first handle element 11d. By a pressure onto the actuating region 52d towards the first handle element 11d, the locking lever 28d is pivoted about the locking bolt 50d and the projecting edge 50d is lifted off the first upper attachment 63d, thus allowing demounting of the first upper attachment 63d. When the first upper attachment 63d has been demounted, the second upper attachment 64d can be demounted.

The securing unit 27d of the handle device 10d comprises a further locking lever 53d, which is arranged on a side of the first handle element 11d that faces away from the locking lever 28d and which fixates the first upper attachment 63d directly on the first handle element 11d in the fixation position. A locking bolt 54d secures the further locking lever 53d to the first handle element 11d. The further locking lever 53d is implemented identically to the first locking lever 28d, also comprising a projecting edge 55d and an actuating region 56d. By pressure onto the actuating region 56d, the further locking lever 53d is pivoted about the locking pin 54d and releases the first upper attachment 63d. For demounting the tool unit 25d, via bilateral pressure on the handle device 10d the actuating regions 52d, 56d are actuated and the locking levers 18d, 53d are pivoted about the locking bolts 50d, 54d into the release positions, thus allowing demounting the first upper attachment 63d and then the second upper attachment 64d. For a complete disassembly of the handle device 10d, the handle elements 11d, 12d may then be separated from each other.

The invention claimed is:

1. A handle device, with a first handle element, a second handle element, a tool unit for holding a tool, a shear joint, which connects the two handle elements pivotably and separably, and a coupling unit, which is configured to keep the two handle elements together counter to a separation direction and which comprises at least one coupling element that is configured to establish, depending on a relative position of the handle elements, a form-fit connection of the handle elements counter to the separation direction, wherein
  the at least one coupling element is embodied as a coupler for centering the form-fit connection,
  the coupling unit further comprises at least one corresponding coupling element, which delimits an at least partly circle-shaped recess for accommodating the at least one coupling element,
  the at least one coupling element and the at least one corresponding coupling element are configured for establishing the form-fit connection via a translational movement in a plane that is at least substantially parallel to a rotary plane of the shear joint,
  the at least one coupling element comprises at least one region having, in a first transverse direction, a first maximum extension and having, in a second transverse direction, a second maximum extension, which is greater than the first maximum extension,
  the first transverse direction and the second transverse direction are transverse to each other and are directions extending, in a mounted state of the at least one coupling element, in a single plane that is perpendicular to a rotary axis of the shear joint, wherein the first maximum extension and the second maximum extension extend in the single plane, wherein the at least one region has, in the single plane, a cross section that is different from a circular cross section,
  the at least one corresponding coupling element delimits a guiding channel for guiding the at least one coupling element into the at least partly circle-shaped recess,
  the at least one coupling element moves through the guiding channel in the translational movement to establish the form-fit connection,
  the second handle element comprises a projection, which is designated to actuate an actuation element of the tool unit, the projection at least partly forms the guiding channel, and in a position of the second handle element relative to the first handle element for establishing the form-fit connection, the second handle element is positioned apart from the tool unit and only contacts the tool unit when rotated around the rotary axis of the shear joint relative to the first handle element after the form-fit connection is established.

2. The handle device according to claim 1, wherein the at least one coupling element is implemented in such a way that it is rounded off at ends of the at least one region.

3. The handle device according to claim 1, wherein the at least one corresponding coupling element forms a further coupler.

4. The handle device according to claim 1, wherein the at least one coupling element and the at least one corresponding coupling element comprise at least one locking unit, which is configured for locking the handle elements in at least one locking position.

5. The handle device according to claim 1, further comprising a securing unit comprising a locking lever which has a pivot axis for pivoting between a release position and a fixation position for the tool unit, the securing unit being configured for reversibly holding the tool unit on at least one of the handle elements, wherein the securing unit comprises a cam mechanism with two inclined planes sliding on one another, which slide off one another to release the tool unit when the locking lever is pivoted into the release position.

6. The handle device according to claim 5, wherein the tool unit comprises a shaft for accommodating a tool, and a stop on which the shaft is supported, and wherein the locking lever is configured to directly fixate the stop on one of the handle elements in the fixation position and to release the stop in the release position.

7. The handle device according to claim 5, wherein the tool unit comprises at least one upper attachment, which forms a tool together with the first handle element and which is in the fixation position fixated to the first handle element by the locking lever.

8. The handle device according to claim 5, wherein the securing unit comprises another locking lever.

9. The handle device according to claim 1, further comprising
a securing unit comprising a locking lever, which has a pivot axis for pivoting between a release position and a fixation position for the tool unit,
the securing unit is configured for reversibly holding the tool unit on at least one of the handle elements, and
the securing unit comprises at least one bolt, which forms a movement axis of the securing unit, and at least one spring element, wherein the at least one spring element secures a restoring force against an opening movement of the securing unit.

* * * * *